(12) United States Patent
Lloyd et al.

(10) Patent No.: US 12,144,928 B2
(45) Date of Patent: Nov. 19, 2024

(54) CANNULA HOLDERS

(71) Applicant: Infection Prevention Products Inc., Chico, CA (US)

(72) Inventors: Meredith Lloyd, Susanville, CA (US); R. Scott Hatfield, Chico, CA (US); Kent Collins, Chico, CA (US)

(73) Assignee: Infection Prevention Products, Inc., Chico, CA (US)

( * ) Notice: Subject to any disclaimer, the term of this patent is extended or adjusted under 35 U.S.C. 154(b) by 0 days.

(21) Appl. No.: 16/732,276

(22) Filed: Dec. 31, 2019

(65) Prior Publication Data

US 2020/0276404 A1    Sep. 3, 2020

Related U.S. Application Data

(63) Continuation of application No. 14/476,127, filed on Sep. 3, 2014, now Pat. No. 10,518,056, which is a
(Continued)

(51) Int. Cl.
*B65D 33/14* (2006.01)
*A61B 50/30* (2016.01)
(Continued)

(52) U.S. Cl.
CPC ......... *A61M 16/0672* (2014.02); *B65D 33/01* (2013.01); *A61B 2050/002* (2016.02);
(Continued)

(58) Field of Classification Search
CPC ........ B65D 33/01; B65D 33/14; A61B 50/36; A61B 2050/002; A61B 2050/314; A61B 2050/316; A61B 2050/318; A61B 50/30
(Continued)

(56) References Cited

U.S. PATENT DOCUMENTS 2,588,695 A    3/1952  Brady et al.
2,883,044 A    4/1959  Kendrick
(Continued)

FOREIGN PATENT DOCUMENTS

RU    2141351 C1    11/1999
RU    2195253 C2    12/2002
(Continued)

OTHER PUBLICATIONS

WO-9711009-A1 (Year: 1997).*
(Continued)

*Primary Examiner* — Jes F Pascua
*Assistant Examiner* — Nina K Attel
(74) *Attorney, Agent, or Firm* — Jinn Su

(57) ABSTRACT

Cannula holders for holding a nasal cannula are described. The cannula holders may also be configured to hold a CPAP mask, BIPAP mask, nebulizer mask, or any other piece of medical equipment. The cannula holders may be used to help prevent a nasal cannula from coming into contact with unclean surfaces when not in use, helping to keep the nasal cannula clean. The cannula holders may help prevent a nasal cannula from falling onto the floor or elsewhere when not in use. The cannula holders provide an alternative to placing or hanging a nasal cannula on equipment, furniture, or elsewhere.

11 Claims, 10 Drawing Sheets

Related U.S. Application Data continuation-in-part of application No. 13/541,723, filed on Jul. 4, 2012, now abandoned.

(60) Provisional application No. 61/653,010, filed on May 30, 2012.

(51) Int. Cl.
*A61M 16/06* (2006.01)
*B65D 33/01* (2006.01)
*A61B 50/00* (2016.01)

(52) U.S. Cl.
CPC .................. *A61B 2050/314* (2016.02); *A61M 2205/6063* (2013.01); *A61M 2209/06* (2013.01); *B65D 33/14* (2013.01)

(58) Field of Classification Search
USPC .......................................................... 383/6, 11
See application file for complete search history.

(56) References Cited

U.S. PATENT DOCUMENTS

| | | | |
|---|---|---|---|
| 3,214,080 A | 10/1965 | Wolfson | |
| RE26,912 E * | 6/1970 | Scheier | D04B 23/08 604/371 |
| 4,193,134 A * | 3/1980 | Hanrahan | A41D 13/015 2/16 |
| 4,519,797 A | 5/1985 | Hall | |
| 5,431,970 A | 7/1995 | Broun et al. | |
| 5,524,802 A | 6/1996 | Benson et al. | |
| 5,715,943 A | 2/1998 | Thompson, Jr. | |
| 5,913,606 A | 6/1999 | Nicholson | |
| 5,964,223 A | 10/1999 | Baran | |
| 5,989,692 A | 11/1999 | Brown | |
| 6,033,392 A * | 3/2000 | Frey | B65D 81/24 206/365 |
| 6,308,875 B1 | 10/2001 | Almo | |
| 6,371,642 B1 | 4/2002 | Nelson et al. | |
| 6,436,085 B1 * | 8/2002 | Lauer | A61M 39/10 604/408 |
| 6,682,247 B1 | 1/2004 | Castillo et al. | |
| 6,711,752 B2 | 3/2004 | Smith | |
| 7,021,825 B1 | 4/2006 | Schultz | |
| 7,533,673 B2 | 5/2009 | Lewis et al. | |
| 7,854,210 B2 | 12/2010 | Moore | |
| 8,361,044 B2 | 1/2013 | Marshall | |
| 8,371,448 B1 * | 2/2013 | Reaux | A61B 46/00 206/570 |
| 8,376,808 B2 * | 2/2013 | Hopkins | A41D 1/22 450/33 |
| 8,454,236 B2 | 6/2013 | Ramirez | |
| 8,777,001 B1 | 7/2014 | Bennett | |
| 8,807,600 B2 | 8/2014 | Hanson | |
| 8,839,955 B1 * | 9/2014 | Klinsport | A46B 17/04 206/362.2 |
| 8,938,898 B2 | 1/2015 | Lo et al. | |
| 2002/0056380 A1 | 5/2002 | Wien et al. | |
| 2003/0056698 A1 | 3/2003 | Comeaux | |
| 2005/0211590 A1 | 9/2005 | McClure et al. | |
| 2005/0241976 A1 | 11/2005 | Britto et al. | |
| 2006/0143767 A1 * | 7/2006 | Yang | B32B 27/12 442/76 |
| 2006/0280385 A1 * | 12/2006 | McGinnis | B65D 33/14 383/22 |
| 2007/0000021 A1 | 2/2007 | Yang et al. | |
| 2007/0131573 A1 | 6/2007 | Boyles | |
| 2007/0180726 A1 | 8/2007 | Harrell | |
| 2008/0295754 A1 | 12/2008 | Moore | |
| 2009/0045095 A1 | 2/2009 | Wagner et al. | |
| 2009/0060397 A1 * | 3/2009 | Allegro, Jr. | B65D 33/20 383/4 |
| 2009/0196896 A1 | 8/2009 | Patton et al. | |
| 2009/0199858 A1 | 8/2009 | Hagberg et al. | |
| 2009/0292258 A1 | 11/2009 | Turner | |
| 2010/0092110 A1 | 4/2010 | Simhony et al. | |
| 2010/0200450 A1 | 8/2010 | Weed | |
| 2010/0270198 A1 | 10/2010 | Wen et al. | |
| 2010/0326765 A1 | 12/2010 | Eddy | |
| 2011/0092935 A1 | 4/2011 | Hann | |
| 2012/0174293 A1 * | 7/2012 | Milliren | A42B 3/10 2/410 |
| 2013/0114915 A1 | 5/2013 | Marom | |
| 2014/0069624 A1 * | 3/2014 | Blackwell | F28F 21/06 427/256 |
| 2015/0089720 A1 * | 4/2015 | Abbey | A42B 3/0473 2/411 |
| 2016/0196770 A1 | 7/2016 | Maher et al. | |
| 2018/0125027 A1 | 5/2018 | Spiers | |

FOREIGN PATENT DOCUMENTS

| | | |
|---|---|---|
| RU | 63583 U1 | 5/2007 |
| SU | 1732953 A1 | 5/1992 |
| WO | WO 1999023966 A1 | 5/1999 |

OTHER PUBLICATIONS

Aquajogger, Mesh Bag, 2009 http://www.aquajogger.com/IW_Products.m4p.pvx?;ITEM?ItemCode=AP50&company=001.
KANGAROOM Storage, Mesh Shower Storage.
PCT application PCT/US2013/043403, Sep. 19, 2013 ISR/WO.
U.S. Appl. No. 13/541,723, Mar. 30, 2015 non-final office action.
U.S. Appl. No. 13/541,723, Sep. 10, 2015 final office action.
U.S. Appl. No. 13/541,723, Jan. 29, 2016 non-final office action.
U.S. Appl. No. 13/541,723, Jul. 13, 2016 final office action.
U.S. Appl. No. 13/541,723, Nov. 28, 2016 non-final office action.
U.S. Appl. No. 13/541,723, May 11, 2017 final office action.
U.S. Appl. No. 13/541,723, Sep. 19, 2017 non-final office action.
U.S. Appl. No. 13/541,723, Feb. 22, 2018 final office action.
U.S. Appl. No. 14/476,127, Nov. 5, 2015 non-final office action.
U.S. Appl. No. 14/476,127, May 5, 2016 final office action.
U.S. Appl. No. 14/476,127, Jan. 13, 2017 non-final office action.
U.S. Appl. No. 14/476,127, Aug. 2, 2017 final office action.
U.S. Appl. No. 14/476,127, Jan. 11, 2019 non-final office action.

* cited by examiner

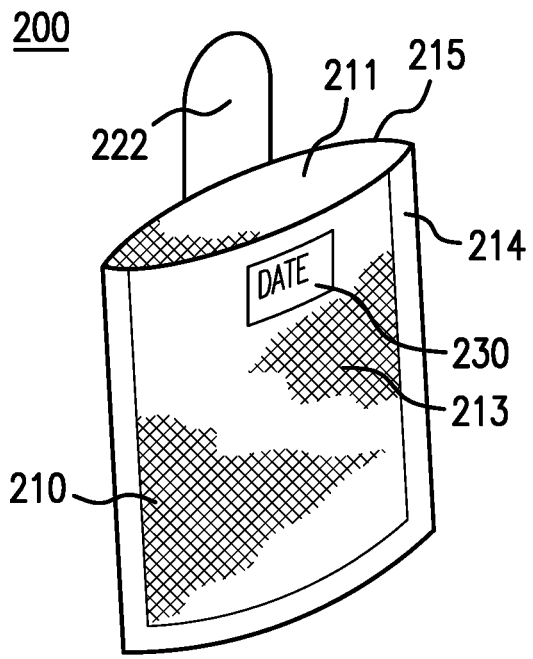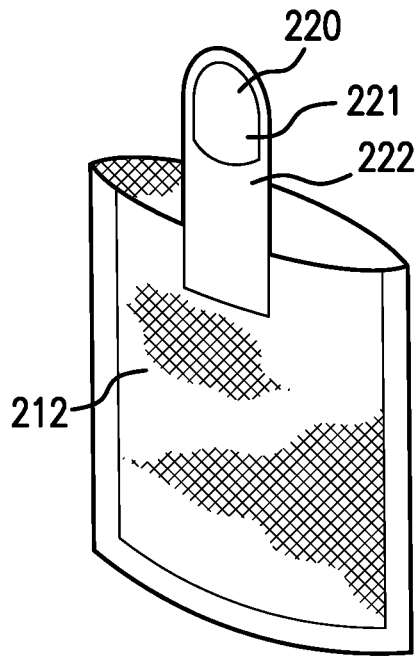
FIG.2A  FIG.2B
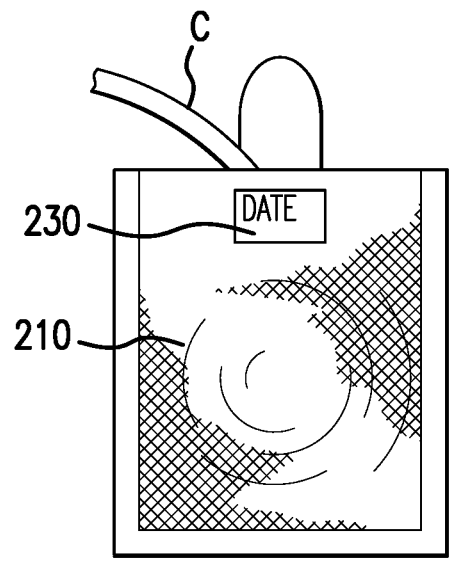
FIG.2C

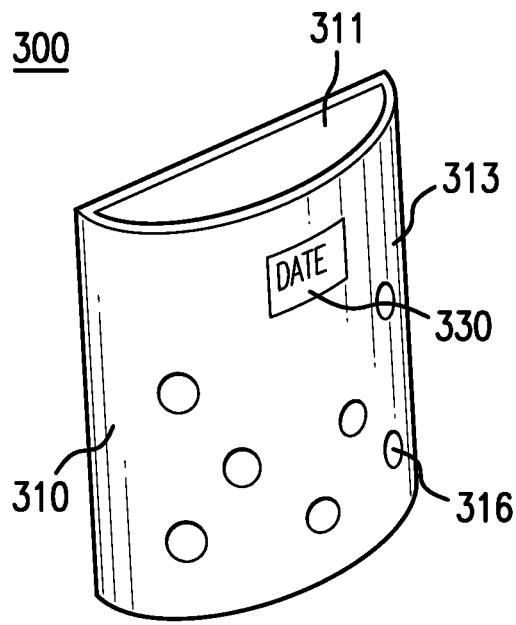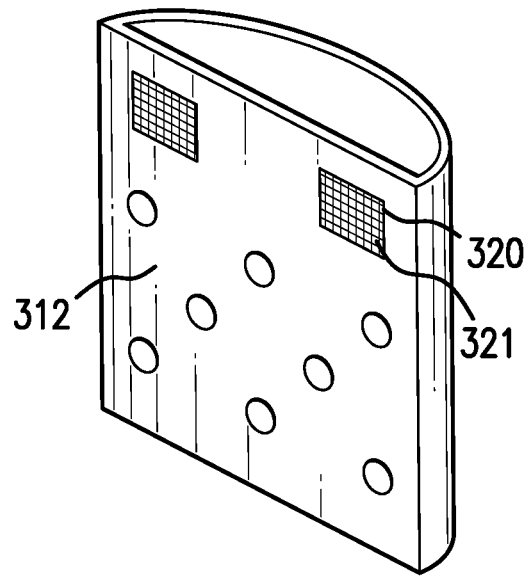
FIG.3A  FIG.3B
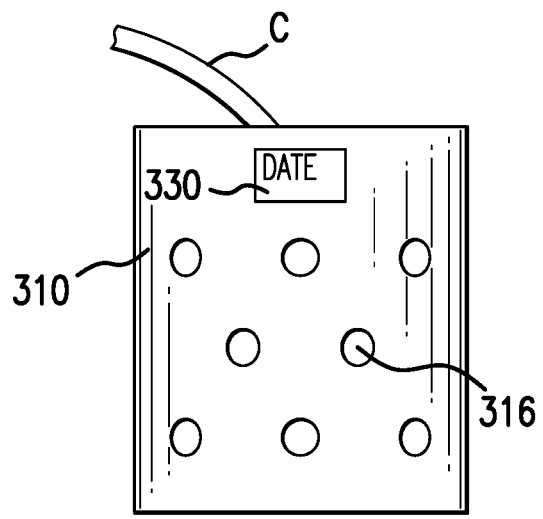
FIG.3C

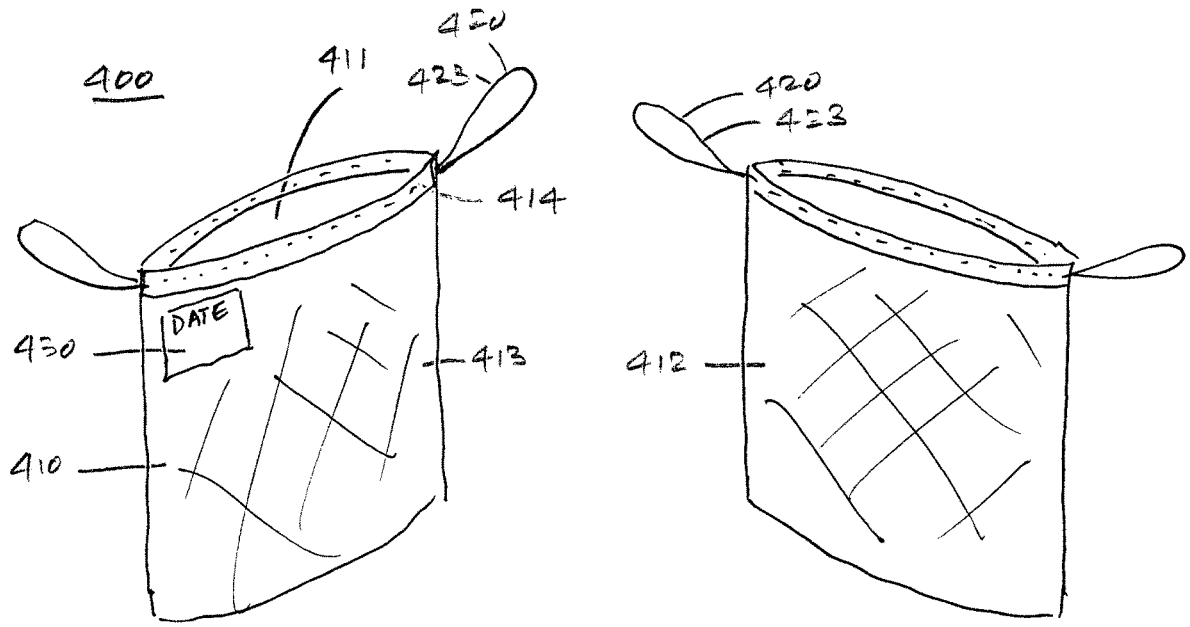
FIG. 4A
FIG. 4B
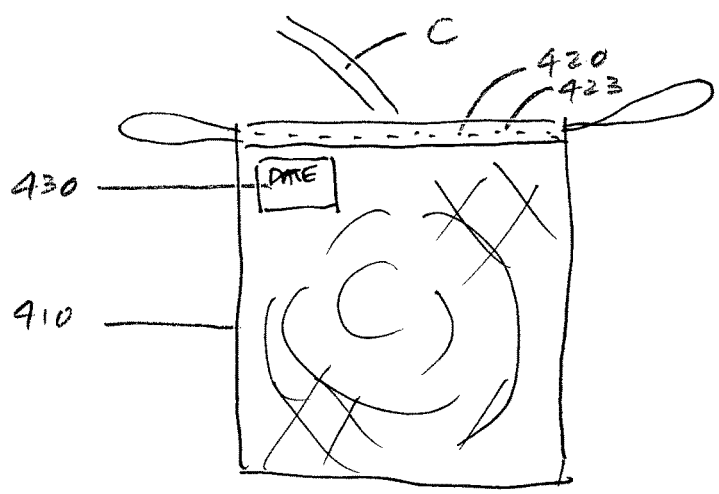
FIG. 4C

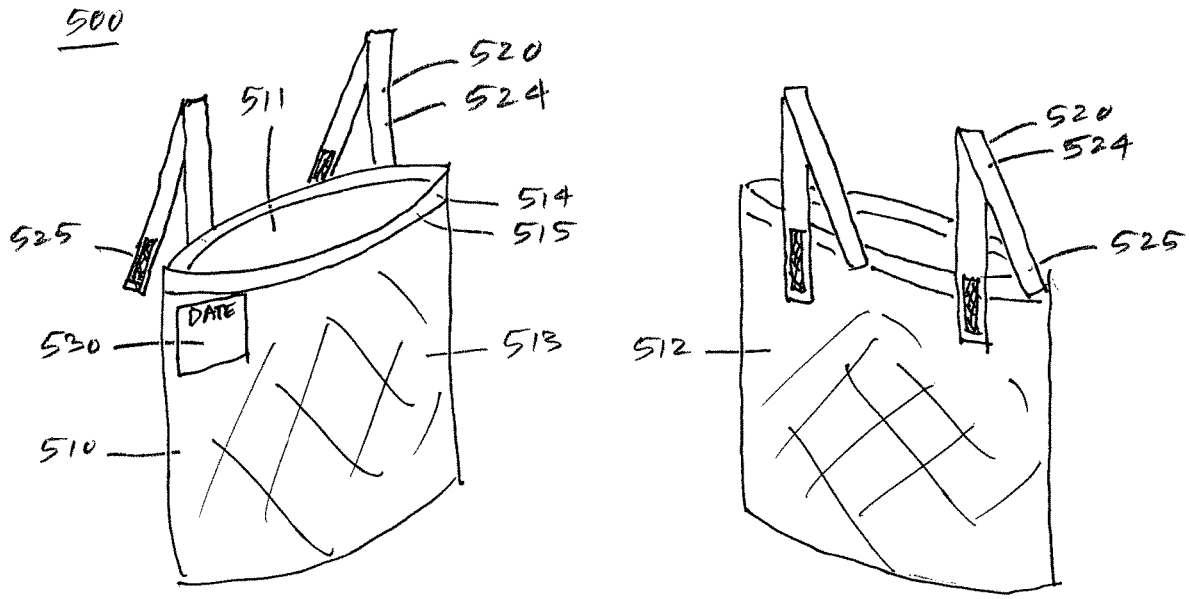
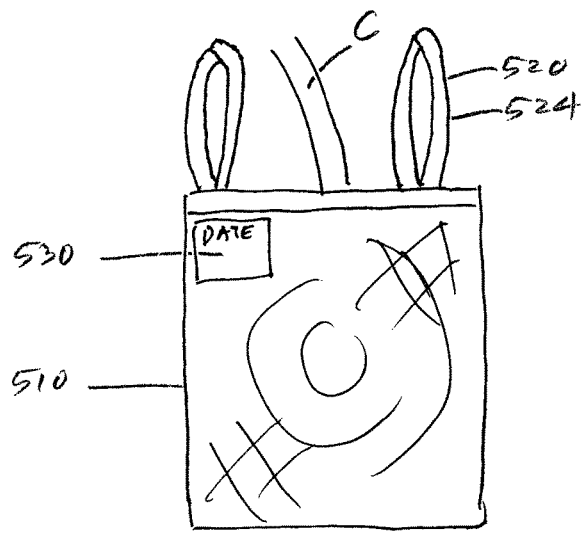
FIG. 5A   FIG. 5B
FIG. 5C

CANNULA HOLDERS

CROSS-REFERENCE TO RELATED APPLICATIONS

This application is a continuation of U.S. patent application Ser. No. 14/476,127, filed Sep. 3, 2014, which is a continuation-in-part of U.S. patent application Ser. No. 13/541,723, filed Jul. 4, 2012, which claims the benefit of U.S. provisional patent application Ser. No. 61/653,010, filed May 30, 2012. The applications listed above are hereby incorporated by reference in their entireties.

BACKGROUND

Nasal cannulas are worn by patients to obtain supplemental oxygen or airflow. A nasal cannula includes a tube worn on the face of a patient and prongs placed in the nostrils of the patient.

A nasal cannula may be temporarily removed from a patient for a variety of reasons. When removed from the patient, a nasal cannula may be placed in a variety of improvised locations. For example, the nasal cannula may be placed on a bed, chair, nightstand, or other furniture. As another example, the nasal cannula may be placed on an oxygen tank valve, monitor, or other piece of equipment. When placed in these locations, the nasal cannula may be exposed to unclean surfaces and become contaminated. In addition, when placed in these locations, the nasal cannula may accidentally fall onto the floor or elsewhere and become contaminated. When the contaminated nasal cannula is placed back on the patient, the chance of infection may increase.

In addition to nasal cannulas, other medical equipment and breathing devices such as CPAP masks, BIPAP masks, and nebulizer masks encounter the same problems of contamination.

What is needed is a device for holding a nasal cannula or other medical equipment when not in use. What is needed is a device which will help prevent a nasal cannula from coming into contact with unclean surfaces when not in use, helping to keep the nasal cannula clean.

SUMMARY

A device for holding a piece of medical equipment is described. The device includes a receptacle configured to hold the piece of medical equipment. The receptacle has an opening, a front surface, and a back surface. The device also includes a coupling element that may be coupled to the back surface of the receptacle. The coupling element may be configured to couple the receptacle to a location. The device may further include a marking surface coupled to the front surface of the receptacle. The marking surface may be configured to be written on with a writing instrument.

A method for holding a piece of medical equipment is described. The method includes providing a receptacle configured to hold the piece of medical equipment, providing a coupling element coupled to a back surface of the receptacle, coupling the receptacle to a location using the coupling element, and inserting the piece of medical equipment into an opening of the receptacle. The method may further include providing a marking surface coupled to a front surface of the receptacle and writing on the marking surface.

BRIEF DESCRIPTION OF DRAWINGS

FIG. 1A shows a front view of cannula holder 100. FIG. 1B shows a rear view of cannula holder 100. FIG. 1C shows cannula holder 100 in use with a nasal cannula C.

FIGS. 2A-2C show one embodiment of a cannula holder 200.

FIG. 2A shows a front view of cannula holder 200. FIG. 2B shows a rear view of cannula holder 200. FIG. 2C shows cannula holder 200 in use with a nasal cannula C.

FIGS. 3A-3C show one embodiment of a cannula holder 300.

FIG. 3A shows a front view of cannula holder 300. FIG. 3B shows a rear view of cannula holder 300. FIG. 3C shows cannula holder 300 in use with a nasal cannula C.

FIGS. 4A-4C show one embodiment of a cannula holder 400.

FIG. 4A shows a front view of cannula holder 400. FIG. 4B shows a rear view of cannula holder 400. FIG. 4C shows cannula holder 400 in use with a nasal cannula C.

FIGS. 5A-5C show one embodiment of a cannula holder 500.

FIG. 5A shows a front view of cannula holder 500. FIG. 5B shows a rear view of cannula holder 500. FIG. 5C shows cannula holder 500 in use with a nasal cannula C.

FIG. 6A shows a front view of cannula holder 600. FIG. 6B shows a rear view of cannula holder 600. FIG. 6C shows cannula holder 600 in use with a nasal cannula C.

FIG. 7A shows the concentration of a bacteria at 5 seconds and 1 hour in receptacles made of six different materials. FIG. 7B shows the concentration of a bacteria at 5 seconds, 1 hour, and 2 hours in receptacles made of spunbond polypropylene fabrics of three different weights. FIGS. 7C-7D show the concentration of a bacteria at 5 seconds, 1 hour, and 2 hours in receptacles made of spunbond polypropylene fabrics from three different manufacturers.

DESCRIPTION

Figures 1A, 1B:
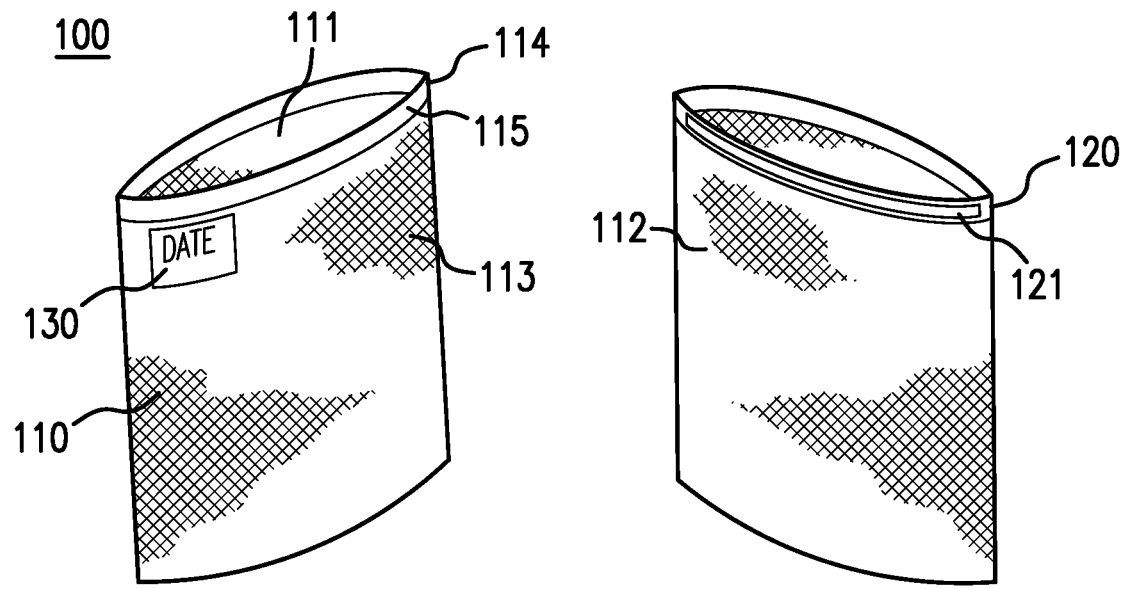
FIGS. 1A-1C show one embodiment of a cannula holder 100.
Figure 1C:
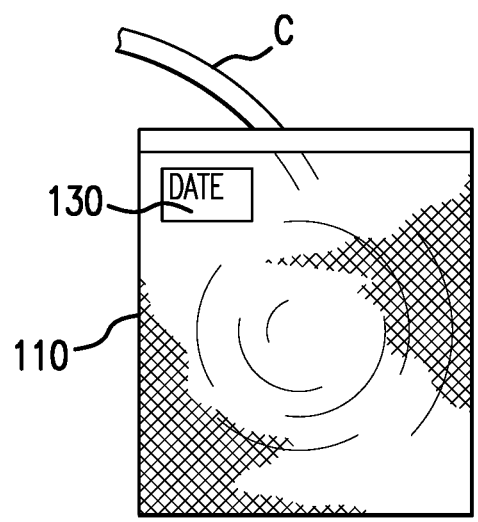

FIGS. 1A-1C show one embodiment of a cannula holder 100.

FIG. 1A shows a front view of cannula holder 100. FIG. 1B shows a rear view of cannula holder 100. FIG. 1C shows cannula holder 100 in use with a nasal cannula.

Cannula holder 100 may be configured to hold a nasal cannula. Cannula holder 100 may also be configured to hold a CPAP mask, BPAP mask, nebulizer mask, or any other piece of medical equipment. Cannula holder 100 is configured to help prevent a nasal cannula from coming into contact with unclean surfaces when not in use, helping to keep the nasal cannula clean. Cannula holder 100 prevents a nasal cannula from falling onto the floor or elsewhere when not in use. Cannula holder 100 provides an alternative to placing or hanging a nasal cannula on equipment, furniture, or elsewhere. Cannula holder 100 may be disposable, or may be cleaned and re-used. Cannula holder 100 may be sterilized using gamma sterilization or other methods, and packaged in sterile packaging and removed when ready to be used.

Cannula holder 100 may include a receptacle 110, one or more coupling elements 120, and one or more marking surfaces 130.

Receptacle 110 may include an opening 111, a back surface 112, and a front surface 113. Opening 111 may be configured to receive a nasal cannula.

Opening 111 may be configured to lay flat when not in use. Alternatively, opening 111 may be configured to remain at least slightly open to facilitate the insertion of a nasal cannula. Opening 111 may be kept at least slightly open with a stiffening element 115 such as a metal or plastic wire coupled at or near opening 111.

Receptacle 110 may be rectangular, semicircular, triangular, or any other suitable shape. Receptacle 110 may be capable of being collapsed flat. Receptacle 110 may be configured to conform to a surface or location to which it is intended to be coupled.

Receptacle 110 may be at least partially made of a fabric or material which is breathable. Receptacle 110 may be at least partially made of a fabric or material which encourages the wicking of moisture away from the medical equipment inside receptacle 110, through capillary action and/or other mechanisms. Receptacle 110 may be at least partially made of a fabric or material which encourages the wicking of moisture from an inside of receptacle 110 to an outside of receptacle 110, through capillary action and/or other mechanisms. Receptacle 110 may be at least partially made of a fabric or material with a low surface energy which reduces or discourages the beading or accumulation of moisture.

Receptacle 110 may be at least partially made of a mesh fabric made of polyester, nylon, cotton, or other suitable fabric. The mesh fabric may be breathable and allow air and moisture to escape. The mesh fabric may have a mesh pattern configured to reduce the likelihood of snagging or catching the nasal cannula, CPAP mask, BPAP mask, nebulizer mask, or any other piece of medical equipment. For example, the mesh fabric may have circular or elliptical openings having a size of approximately 0.5 mm to 1.5 mm, with an open area of approximately 30-50%. The mesh fabric may have a mesh pattern and/or color that allows the contents of receptacle 110 to be at least partially visible. The mesh fabric may be a single layer, double layer, triple layer, or any other suitable type of weave that allows airflow but reduces the possibility of snagging on the medical equipment inserted into receptacle 110. The mesh fabric may be made of a material that does not substantially weaken when exposed to moisture. The mesh fabric may be of a weight that is light, medium, heavy, or any suitable combination of weights.

The mesh fabric may be treated with an antimicrobial agent capable of inhibiting the growth of and/or kill microorganisms. The antimicrobial agent may include silver or any other suitable antimicrobial agent. The silver may be in the form of silver nanoparticles bound in a zeolite, calcium carbonate, ceramic, or other suitable matrix, applied to the mesh fabric. The mesh fabric may have inherent antimicrobial properties. The mesh fabric may be treated with hydrophobic, hydrophilic, or other treatments.

Receptacle 110 may be at least partially made of one or more nonwoven fabrics. These fabrics may include spunbond polypropylene fabrics available from DuPont, Surya Textech, Oxco, and others. The polypropylene fabrics may be 100% polypropylene or a polypropylene blend. In one embodiment, a polypropylene blend may include approximately 63% polypropylene, 23% polyethylene terephthalate (PET), 8% viscose fiber, 2% acrylic acid, 1.5% polyamide, and 2.5% other materials. In one embodiment, a polypropylene fabric used may have a weight from approximately 20 GSM to 100 GSM.

Alternatively, receptacle 110 may be at least partially made of a plastic, paper/cellulose, metal, or any other suitable material. Receptacle 110 may be at least partially made of a material that is perforated or non-perforated. Receptacle 110 may be at least partially made of a flexible or rigid material. Any of these materials may be treated with an antimicrobial agent.

Receptacle 110 may be reinforced with a trim 114 along opening 111 and/or one or more edges. Trim 114 may be formed by folding over the fabric one or more times and stitched, glued, ultrasonically welded, and/or otherwise coupled to itself. Alternatively, trim 114 may be a separate piece of fabric. Opening 111 may be kept at least slightly open by shaping trim 114.

Receptacle 110 may be configured to hold a nasal cannula. Receptacle 110 may be configured to enclose all, half, or any portion of a nasal cannula. Receptacle 110 may also be configured to hold a CPAP mask, BPAP mask, nebulizer mask, or any other piece of medical equipment. In one embodiment, receptacle 110 may have a length of approximately 4-15 inches and a width of approximately 4-15 inches. Receptacle 110 may be configured to be breathable to allow for the passage of air to facilitate drying of the nasal cannula or other medical equipment. Receptacle 110 may be configured to inhibit the growth of microbes on a piece of medical equipment placed in receptacle 110.

Coupling element 120 may be coupled to back surface 112 of receptacle 110. Alternatively, coupling element 120 may be coupled to front surface 113 of receptacle 110, or any suitable portion of receptacle 110.

Coupling element 120 may include an adhesive tape 121 with a removable backing, such as a double-sided adhesive tape or other suitable tape. Adhesive tape 121 may be configured to adhere to a surface and be strong enough to hold a piece of medical equipment, yet be easily removed from the surface without leaving a residue or becoming separated from back surface 112 of receptacle 110. Alternatively, coupling element 120 may include one or more hook-and-loop fasteners, magnets, straps, hooks, rigid or flexible handles, or other suitable coupling elements.

Coupling element 120 may be configured to couple receptacle 110 securely to an oxygen tank, oxygen concentrator, wall, rail, or any other suitable location. Coupling element 120 may be configured to hold up to 2 pounds, up to 3 pounds, up to 4 pounds, or up to 5 pounds. Coupling element 120 may be configured to be easily removed. Coupling element 120 may be one-time use or reusable. Coupling element 120 may be detachable from receptacle 110.

Marking surface 130 may be coupled to front surface 113 of receptacle 110. Alternatively, marking surface 130 may be coupled to back surface 112 of receptacle, or any suitable portion of receptacle 110. Marking surface 130 may be written on with a pen or other writing instrument. Marking surface 130 may include an ink, coating, or material applied to at least a portion of receptacle 110. Marking surface 130 may include a writable ink, a rubberized or plasticized coating, or other material applied to at least a portion of receptacle 110. Alternatively, marking surface 130 may include a label made of paper, fabric, or other suitable material stitched, glued, taped, or otherwise coupled to receptacle 110. Still alternatively, marking surface 130 may include a hang tag tied with a string or otherwise coupled to receptacle 110. Still alternatively, marking surface 130 may be a substantially smooth portion of receptacle 110. Marking surface 130 may be pre-marked with a mark such as "DATE," "NAME," or any other suitable mark.

Marking surface 130 may allow a date to be written on receptacle 110. Marking surface 130 may help indicate for how long a nasal cannula and/or cannula holder 100 has been in use, and may help act as a reminder that a new nasal cannula and/or cannula holder 100 is needed. Marking surface 130 may also allow patient name or any other information to be written on receptacle 110.

FIGS. 2A-2C show one embodiment of a cannula holder 200.

FIG. 2A shows a front view of cannula holder 200. FIG. 2B shows a rear view of cannula holder 200. FIG. 2C shows cannula holder 200 in use with a nasal cannula.

Cannula holder 200 may be configured to hold a nasal cannula. Cannula holder 200 may also be configured to hold a CPAP mask, BPAP mask, nebulizer mask, or any other piece of medical equipment. Cannula holder 200 is configured to help prevent a nasal cannula from coming into contact with unclean surfaces when not in use, helping to keep the nasal cannula clean. Cannula holder 200 prevents a nasal cannula from falling onto the floor or elsewhere when not in use. Cannula holder 200 provides an alternative to placing or hanging a nasal cannula on equipment, furniture, or elsewhere. Cannula holder 200 may be disposable, or may be cleaned and re-used. Cannula holder 200 may be sterilized using gamma sterilization or other methods, and packaged in sterile packaging and removed when ready to be used.

Cannula holder 200 may include a receptacle 210, one or more coupling elements 220, and one or more marking surfaces 230.

Receptacle 210 may include an opening 211, a back surface 212, and a front surface 213. Opening 211 may be configured to receive a nasal cannula.

Opening 211 may be configured to lay flat when not in use. Alternatively, opening 211 may be configured to remain at least slightly open to facilitate the insertion of a nasal cannula. Opening 211 may be kept at least slightly open with a stiffening element 215 such as a metal or plastic wire coupled at or near opening 211.

Receptacle 210 may be rectangular, semicircular, triangular, or any other suitable shape. Receptacle 210 may be capable of being collapsed flat. Receptacle 210 may be configured to conform to a surface or location to which it is intended to be coupled.

Receptacle 210 may be at least partially made of a fabric or material which is breathable. Receptacle 210 may be at least partially made of a fabric or material which encourages the wicking of moisture away from the medical equipment inside receptacle 210, through capillary action and/or other mechanisms. Receptacle 210 may be at least partially made of a fabric or material which encourages the wicking of moisture from an inside of receptacle 210 to an outside of receptacle 210, through capillary action and/or other mechanisms. Receptacle 210 may be at least partially made of a fabric or material with a low surface energy which reduces or discourages the beading or accumulation of moisture.

Receptacle 210 may be at least partially made of a mesh fabric made of polyester, nylon, cotton, or other suitable fabric. The mesh fabric may be breathable and allow air and moisture to escape. The mesh fabric may have a mesh pattern configured to reduce the likelihood of snagging or catching the nasal cannula, CPAP mask, BPAP mask, nebulizer mask, or any other piece of medical equipment. For example, the mesh fabric may have circular or elliptical openings having a size of approximately 0.5 mm to 1.5 mm, with an open area of approximately 30-50%. The mesh fabric may have a mesh pattern and/or color that allows the contents of receptacle 210 to be at least partially visible. The mesh fabric may be a single layer, double layer, triple layer, or any other suitable type of weave that allows airflow but reduces the possibility of snagging on the medical equipment inserted into receptacle 210. The mesh fabric may be made of a material that does not substantially weaken when exposed to moisture. The mesh fabric may be of a weight that is light, medium, heavy, or any suitable combination of weights.

The mesh fabric may be treated with an antimicrobial agent capable of inhibiting the growth of and/or kill microorganisms. The antimicrobial agent may include silver or any other suitable antimicrobial agent. The silver may be in the form of silver nanoparticles bound in a zeolite, calcium carbonate, ceramic, or other suitable matrix, applied to the mesh fabric. The mesh fabric may have inherent antimicrobial properties. The mesh fabric may be treated with hydrophobic, hydrophilic, or other treatments.

Receptacle 210 may be at least partially made of one or more nonwoven fabrics. These fabrics may include spunbond polypropylene fabrics available from DuPont, Surya Textech, Oxco, and others. The polypropylene fabrics may be 100% polypropylene or a polypropylene blend. In one embodiment, a polypropylene blend may include approximately 63% polypropylene, 23% polyethylene terephthalate (PET), 8% viscose fiber, 2% acrylic acid, 1.5% polyamide, and 2.5% other materials. In one embodiment, a polypropylene fabric used may have a weight from approximately 20 GSM to 100 GSM.

Alternatively, receptacle 210 may be at least partially made of a plastic, paper/cellulose, metal, or any other suitable material. Receptacle 210 may be at least partially made of a material that is perforated or non-perforated. Receptacle 210 may be at least partially made of a flexible or rigid material. Any of these materials may be treated with an antimicrobial agent.

Receptacle 210 may be reinforced with a trim 214 along opening 211 and/or one or more edges. Trim 214 may be formed by folding over the fabric one or more times and stitched, glued, ultrasonically welded, and/or otherwise coupled to itself. Alternatively, trim 214 may be a separate piece of fabric. Opening 211 may be kept at least slightly open by shaping trim 214.

Receptacle 210 may be configured to hold a nasal cannula. Receptacle 210 may be configured to enclose all, half, or any portion of a nasal cannula. Receptacle 210 may also be configured to hold a CPAP mask, BPAP mask, nebulizer mask, or any other piece of medical equipment. In one embodiment, receptacle 210 may have a length of approximately 4-15 inches and a width of approximately 4-15 inches. Receptacle 210 may be configured to be breathable to allow for the passage of air to facilitate drying of the nasal cannula or other medical equipment. Receptacle 210 may be configured to inhibit the growth of microbes on a piece of medical equipment placed in receptacle 210.

Coupling element 220 may be coupled to a hanging tab 222 coupled to back surface 212 of receptacle 210. Alternatively, coupling element 220 may be coupled to back surface 212 of receptacle 210, front surface 213 of receptacle 210, or any suitable portion of receptacle 210.

Coupling element 220 may include an adhesive tape 221 with a removable backing, such as a double-sided adhesive tape or other suitable tape. Adhesive tape 221 may be configured to adhere to a surface and be strong enough to hold a piece of medical equipment, yet be easily removed from the surface without leaving a residue or becoming separated from hanging tab 222. Alternatively, coupling element 220 may include one or more hook-and-loop fasteners, magnets, straps, hooks, rigid or flexible handles, or other suitable coupling elements coupled to hanging tab 222.

Coupling element 220 may be configured to couple receptacle 210 securely to an oxygen tank, oxygen concentrator, wall, rail, or any other suitable location. Coupling element 220 may be configured to hold up to 2 pounds, up to 3 pounds, up to 4 pounds, or up to 5 pounds. Coupling element 220 may be configured to be easily removed. Coupling element 220 may be one-time use or reusable. Coupling element 220 may be detachable from receptacle 210. Marking surface 230 may be coupled to front surface 213 of receptacle 210. Alternatively, marking surface 230 may be coupled to back surface 212 of receptacle, or any suitable portion of receptacle 210. Marking surface 230 may be written on with a pen or other writing instrument. Marking surface 230 may include an ink, coating, or material applied to at least a portion of receptacle 210. Marking surface 230 may include a writable ink, a rubberized or plasticized coating, or other material applied to at least a portion of receptacle 210. Alternatively, marking surface 230 may include a label made of paper, fabric, or other suitable material stitched, glued, taped, or otherwise coupled to receptacle 210. Still alternatively, marking surface 230 may include a hang tag tied with a string or otherwise coupled to receptacle 210. Still alternatively, marking surface 230 may be a substantially smooth portion of receptacle 210. Marking surface 230 may be pre-marked with a mark such as "DATE," "NAME," or any other suitable mark.

Marking surface 230 may allow a date to be written on receptacle 210. Marking surface 230 may help indicate for how long a nasal cannula and/or cannula holder 200 has been in use, and may help act as a reminder that a new nasal cannula and/or cannula holder 200 is needed. Marking surface 230 may also allow patient name or any other information to be written on receptacle 210.

FIGS. 3A-3C show one embodiment of a cannula holder 300. FIG. 3A shows a front view of cannula holder 300. FIG. 3B shows a rear view of cannula holder 300. FIG. 3C shows cannula holder 300 in use with a nasal cannula.

Cannula holder 300 may be configured to hold a nasal cannula. Cannula holder 300 may also be configured to hold a CPAP mask, BPAP mask, nebulizer mask, or any other piece of medical equipment. Cannula holder 300 is configured to help prevent a nasal cannula from coming into contact with unclean surfaces when not in use, helping to keep the nasal cannula clean. Cannula holder 300 prevents a nasal cannula from falling onto the floor or elsewhere when not in use. Cannula holder 300 provides an alternative to placing or hanging a nasal cannula on equipment, furniture, or elsewhere. Cannula holder 300 may be disposable, or may be cleaned and re-used. Cannula holder 300 may be sterilized using gamma sterilization or other methods, and packaged in sterile packaging and removed when ready to be used.

Cannula holder 300 may include a receptacle 310, one or more coupling elements 320, and one or more marking surfaces 330.

Receptacle 310 may include an opening 311, a back surface 312, and a front surface 313. Opening 311 may be configured to receive a nasal cannula.

Receptacle 310 may be rectangular, semicircular, triangular, or any other suitable shape. Receptacle 310 may be capable of being stacked. Receptacle 310 may be configured to conform to a surface or location to which it is intended to be coupled.

Receptacle 310 may be at least partially made of a material which is breathable. Receptacle 310 may be at least partially made of a material which encourages the wicking of moisture away from the medical equipment inside receptacle 310, through capillary action and/or other mechanisms. Receptacle 310 may be at least partially made of a material which encourages the wicking of moisture from an inside of receptacle 310 to an outside of receptacle 310, through capillary action and/or other mechanisms. Receptacle 310 may be at least partially made of a material with a low surface energy which reduces or discourages the beading or accumulation of moisture.

Receptacle 310 may be at least partially made of a substantially rigid material such as plastic, metal, or other suitable material.

Receptacle 310 may be treated with an antimicrobial agent capable of inhibiting the growth of and/or kill microorganisms. The antimicrobial agent may include silver or any other suitable antimicrobial agent.

Receptacle 310 may be configured to hold a nasal cannula. Receptacle 310 may be configured to enclose all, half, or any portion of a nasal cannula. Receptacle 310 may also be configured to hold a CPAP mask, BPAP mask, nebulizer mask, or any other piece of medical equipment. In one embodiment, receptacle 310 may have a length of approximately 4-15 inches, a width of approximately 4-15 inches, and a depth of approximately 1-3 in. Receptacle 310 may include one or more perforations or holes 316 to allow for the passage of air to facilitate drying of the nasal cannula or other medical equipment. Receptacle 310 may be configured to inhibit the growth of microbes on a piece of medical equipment placed in receptacle 310.

Coupling element 320 may be coupled to back surface 312 of receptacle 310. Alternatively, coupling element 320 may be coupled to front surface 313 of receptacle 310, or any suitable portion of receptacle 310.

Coupling element 320 may include an adhesive tape 321 with a removable backing, such as a double-sided adhesive tape or other suitable tape. Adhesive tape 321 may be configured to adhere to a surface and be strong enough to hold a piece of medical equipment, yet be easily removed from the surface without leaving a residue or becoming separated from back surface 312 of receptacle 310. Alternatively, coupling element 320 may include one or more hook-and-loop fasteners, magnets, straps, hooks, rigid or flexible handles, or other suitable coupling elements.

Coupling element 320 may be configured to couple receptacle 310 securely to an oxygen tank, oxygen concentrator, wall, rail, or any other suitable location. Coupling element 320 may be configured to hold up to 2 pounds, up to 3 pounds, up to 4 pounds, or up to 5 pounds. Coupling element 320 may be configured to be easily removed. Coupling element 320 may be one-time use or reusable. Coupling element 320 may be detachable from receptacle 310.

Marking surface 330 may be coupled to front surface 313 of receptacle 310. Alternatively, marking surface 330 may be coupled to back surface 312 of receptacle, or any suitable portion of receptacle 310. Marking surface 330 may be written on with a pen or other writing instrument. Marking surface 330 may include an ink, coating, or material applied to at least a portion of receptacle 310. Marking surface 330 may include a writable ink, a rubberized or plasticized coating, or other material applied to at least a portion of receptacle 310. Alternatively, marking surface 330 may include a label made of paper, fabric, or other suitable material stitched, glued, taped, or otherwise coupled to receptacle 310. Still alternatively, marking surface 330 may include a hang tag tied with a string or otherwise coupled to receptacle 310. Still alternatively, marking surface 330 may be a substantially smooth portion of receptacle 310. Marking surface 330 may be pre-marked with a mark such as "DATE," "NAME," or any other suitable mark.

Marking surface 330 may allow a date to be written on receptacle 310. Marking surface 330 may help indicate for how long a nasal cannula and/or cannula holder 300 has been in use, and may help act as a reminder that a new nasal cannula and/or cannula holder 300 is needed. Marking surface 330 may also allow patient name or any other information to be written on receptacle 310.

FIGS. 4A-4C show one embodiment of a cannula holder 400.

FIG. 4A shows a front view of cannula holder 400. FIG. 4B shows a rear view of cannula holder 400. FIG. 4C shows cannula holder 400 in use with a nasal cannula.

Cannula holder 400 may be configured to hold a nasal cannula. Cannula holder 400 may also be configured to hold a CPAP mask, BPAP mask, nebulizer mask, or any other piece of medical equipment. Cannula holder 400 is configured to help prevent a nasal cannula from coming into contact with unclean surfaces when not in use, helping to keep the nasal cannula clean. Cannula holder 400 prevents a nasal cannula from falling onto the floor or elsewhere when not in use. Cannula holder 400 provides an alternative to placing or hanging a nasal cannula on equipment, furniture, or elsewhere. Cannula holder 400 may be disposable, or may be cleaned and re-used. Cannula holder 400 may be sterilized using gamma sterilization or other methods, and packaged in sterile packaging and removed when ready to be used.

Cannula holder 400 may include a receptacle 410, one or more coupling elements 420, and one or more marking surfaces 430.

Receptacle 410 may include an opening 411, a back surface 412, and a front surface 413. Opening 411 may be configured to receive a nasal cannula.

Opening 411 may be configured to lay flat when not in use. Alternatively, opening 411 may be configured to remain at least slightly open to facilitate the insertion of a nasal cannula.

Receptacle 410 may be rectangular, semicircular, triangular, or any other suitable shape. Receptacle 410 may be capable of being collapsed flat. Receptacle 410 may be configured to conform to a surface or location to which it is intended to be coupled.

Receptacle 410 may be at least partially made of a fabric or material which is breathable. Receptacle 410 may be at least partially made of a fabric or material which encourages the wicking of moisture away from the medical equipment inside receptacle 410, through capillary action and/or other mechanisms. Receptacle 410 may be at least partially made of a fabric or material which encourages the wicking of moisture from an inside of receptacle 410 to an outside of receptacle 410, through capillary action and/or other mechanisms. Receptacle 410 may be at least partially made of a fabric or material with a low surface energy which reduces or discourages the beading or accumulation of moisture.

Receptacle 410 may be at least partially made of a mesh fabric made of polyester, nylon, cotton, or other suitable fabric. The mesh fabric may be breathable and allow air and moisture to escape. The mesh fabric may have a mesh pattern configured to reduce the likelihood of snagging or catching the nasal cannula, CPAP mask, BPAP mask, nebulizer mask, or any other piece of medical equipment. For example, the mesh fabric may have circular or elliptical openings having a size of approximately 0.5 mm to 1.5 mm, with an open area of approximately 30-50%. The mesh fabric may have a mesh pattern and/or color that allows the contents of receptacle 410 to be at least partially visible. The mesh fabric may be a single layer, double layer, triple layer, or any other suitable type of weave that allows airflow but reduces the possibility of snagging on the medical equipment inserted into receptacle 410. The mesh fabric may be made of a material that does not substantially weaken when exposed to moisture. The mesh fabric may be of a weight that is light, medium, heavy, or any suitable combination of weights.

The mesh fabric may be treated with an antimicrobial agent capable of inhibiting the growth of and/or kill microorganisms. The antimicrobial agent may include silver or any other suitable antimicrobial agent. The silver may be in the form of silver nanoparticles bound in a zeolite, calcium carbonate, ceramic, or other suitable matrix, applied to the mesh fabric. The mesh fabric may have inherent antimicrobial properties. The mesh fabric may be treated with hydrophobic, hydrophilic, or other treatments.

Receptacle 410 may be at least partially made of one or more nonwoven fabrics. These fabrics may include spunbond polypropylene fabrics available from DuPont, Surya Textech, Oxco, and others. The polypropylene fabrics may be 100% polypropylene or a polypropylene blend. In one embodiment, a polypropylene blend may include approximately 63% polypropylene, 23% polyethylene terephthalate (PET), 8% viscose fiber, 2% acrylic acid, 1.5% polyamide, and 2.5% other materials. In one embodiment, a polypropylene fabric used may have a weight from approximately 20 GSM to 100 GSM.

Alternatively, receptacle 410 may be at least partially made of a plastic, paper/cellulose, metal, or any other suitable material. Receptacle 410 may be at least partially made of a material that is perforated or non-perforated. Receptacle 410 may be at least partially made of a flexible or rigid material. Any of these materials may be treated with an antimicrobial agent.

Receptacle 410 may be reinforced with a trim 414 along opening 411 and/or one or more edges. Trim 414 may be formed by folding over the fabric one or more times and stitched, glued, ultrasonically welded, and/or otherwise coupled to itself. Alternatively, trim 414 may be a separate piece of fabric. Opening 411 may be kept at least slightly open by shaping trim 414.

Receptacle 410 may be configured to hold a nasal cannula. Receptacle 410 may be configured to enclose all, half, or any portion of a nasal cannula. Receptacle 410 may also be configured to hold a CPAP mask, BPAP mask, nebulizer mask, or any other piece of medical equipment. In one embodiment, receptacle 410 may have a length of approximately 4-15 inches and a width of approximately 4-15 inches. Receptacle 410 may be configured to be breathable to allow for the passage of air to facilitate drying of the nasal cannula or other medical equipment. Receptacle 410 may be configured to inhibit the growth of microbes on a piece of medical equipment placed in receptacle 410.

Coupling element 420 may include a drawstring 423 coupled at or near at least a portion of opening 411 of receptacle 410. Drawstring 423 may be threaded or passed through a portion of receptacle 410 such as trim 414 formed at or near opening 411 of receptacle 410. Drawstring 423 may extend from one or both sides or ends of receptacle 410. Drawstring 423 may be cinched and loosened to at least partially close and open opening 411 of receptacle 410.

Coupling element 420 may be configured to allow receptacle 410 to be hung from an oxygen tank, oxygen concentrator, rail, or any other suitable location. Coupling element 420 may be configured to hold up to 2 pounds, up to 3 pounds, up to 4 pounds, or up to 5 pounds. Coupling element 420 may be configured to be easily removed. Coupling element 420 may be reusable. Coupling element 420 may be detachable from receptacle 410.

Marking surface 430 may be coupled to front surface 413 of receptacle 410. Alternatively, marking surface 430 may be coupled to back surface 412 of receptacle, or any suitable portion of receptacle 410. Marking surface 430 may be written on with a pen or other writing instrument. Marking surface 430 may include an ink, coating, or material applied to at least a portion of receptacle 410. Marking surface 430 may include a writable ink, a rubberized or plasticized coating, or other material applied to at least a portion of receptacle 410. Alternatively, marking surface 430 may include a label made of paper, fabric, or other suitable material stitched, glued, taped, or otherwise coupled to receptacle 410. Still alternatively, marking surface 430 may include a hang tag tied with a string or otherwise coupled to receptacle 410. Still alternatively, marking surface 430 may be a substantially smooth portion of receptacle 410. Marking surface 430 may be pre-marked with a mark such as "DATE," "NAME," or any other suitable mark.

Marking surface 430 may allow a date to be written on receptacle 410. Marking surface 430 may help indicate for how long a nasal cannula and/or cannula holder 400 has been in use, and may help act as a reminder that a new nasal cannula and/or cannula holder 400 is needed. Marking surface 430 may also allow patient name or any other information to be written on receptacle 410.

FIGS. 5A-5C show one embodiment of a cannula holder 500. FIG. 5A shows a front view of cannula holder 500. FIG. 5B shows a rear view of cannula holder 500. FIG. 5C shows cannula holder 500 in use with a nasal cannula.

Cannula holder 500 may be configured to hold a nasal cannula. Cannula holder 500 may also be configured to hold a CPAP mask, BPAP mask, nebulizer mask, or any other piece of medical equipment. Cannula holder 500 is configured to help prevent a nasal cannula from coming into contact with unclean surfaces when not in use, helping to keep the nasal cannula clean. Cannula holder 500 prevents a nasal cannula from falling onto the floor or elsewhere when not in use. Cannula holder 500 provides an alternative to placing or hanging a nasal cannula on equipment, furniture, or elsewhere. Cannula holder 500 may be disposable, or may be cleaned and re-used. Cannula holder 500 may be sterilized using gamma sterilization or other methods, and packaged in sterile packaging and removed when ready to be used.

Cannula holder 500 may include a receptacle 510, one or more coupling elements 520, and one or more marking surfaces 530.

Receptacle 510 may include an opening 511, a back surface 512, and a front surface 513. Opening 511 may be configured to receive a nasal cannula.

Opening 511 may be configured to lay flat when not in use. Alternatively, opening 511 may be configured to remain at least slightly open to facilitate the insertion of a nasal cannula. Opening 511 may be kept at least slightly open with a stiffening element 515 such as a metal or plastic wire coupled at or near opening 511.

Receptacle 510 may be rectangular, semicircular, triangular, or any other suitable shape. Receptacle 510 may be capable of being collapsed flat. Receptacle 510 may be configured to conform to a surface or location to which it is intended to be coupled.

Receptacle 510 may be at least partially made of a fabric or material which is breathable. Receptacle 510 may be at least partially made of a fabric or material which encourages the wicking of moisture away from the medical equipment inside receptacle 510, through capillary action and/or other mechanisms. Receptacle 510 may be at least partially made of a fabric or material which encourages the wicking of moisture from an inside of receptacle 510 to an outside of receptacle 510, through capillary action and/or other mechanisms. Receptacle 510 may be at least partially made of a fabric or material with a low surface energy which reduces or discourages the beading or accumulation of moisture.

Receptacle 510 may be at least partially made of a mesh fabric made of polyester, nylon, cotton, or other suitable fabric. The mesh fabric may be breathable and allow air and moisture to escape. The mesh fabric may have a mesh pattern configured to reduce the likelihood of snagging or catching the nasal cannula, CPAP mask, BPAP mask, nebulizer mask, or any other piece of medical equipment. For example, the mesh fabric may have circular or elliptical openings having a size of approximately 0.5 mm to 1.5 mm, with an open area of approximately 30-50%. The mesh fabric may have a mesh pattern and/or color that allows the contents of receptacle 510 to be at least partially visible. The mesh fabric may be a single layer, double layer, triple layer, or any other suitable type of weave that allows airflow but reduces the possibility of snagging on the medical equipment inserted into receptacle 510. The mesh fabric may be made of a material that does not substantially weaken when exposed to moisture. The mesh fabric may be of a weight that is light, medium, heavy, or any suitable combination of weights.

The mesh fabric may be treated with an antimicrobial agent capable of inhibiting the growth of and/or kill microorganisms. The antimicrobial agent may include silver or any other suitable antimicrobial agent. The silver may be in the form of silver nanoparticles bound in a zeolite, calcium carbonate, ceramic, or other suitable matrix, applied to the mesh fabric. The mesh fabric may have inherent antimicrobial properties. The mesh fabric may be treated with hydrophobic, hydrophilic, or other treatments.

Receptacle 510 may be at least partially made of one or more nonwoven fabrics. These fabrics may include spunbond polypropylene fabrics available from DuPont, Surya Textech, Oxco, and others. The polypropylene fabrics may be 100% polypropylene or a polypropylene blend. In one embodiment, a polypropylene blend may include approximately 63% polypropylene, 23% polyethylene terephthalate (PET), 8% viscose fiber, 2% acrylic acid, 1.5% polyamide, and 2.5% other materials. In one embodiment, a polypropylene fabric used may have a weight from approximately 20 GSM to 100 GSM.

Alternatively, receptacle 510 may be at least partially made of a plastic, paper/cellulose, metal, or any other suitable material. Receptacle 510 may be at least partially made of a material that is perforated or non-perforated. Receptacle 510 may be at least partially made of a flexible or rigid material. Any of these materials may be treated with an antimicrobial agent.

Receptacle 510 may be reinforced with a trim 514 along opening 511 and/or one or more edges. Trim 514 may be formed by folding over the fabric one or more times and stitched, glued, ultrasonically welded, and/or otherwise coupled to itself. Alternatively, trim 514 may be a separate piece of fabric. Opening 511 may be kept at least slightly open by shaping trim 514.

Receptacle 510 may be configured to hold a nasal cannula. Receptacle 510 may be configured to enclose all, half, or any portion of a nasal cannula. Receptacle 510 may also be configured to hold a CPAP mask, BPAP mask, nebulizer mask, or any other piece of medical equipment. In one embodiment, receptacle 510 may have a length of approximately 4-15 inches and a width of approximately 4-15 inches. Receptacle 510 may be configured to be breathable to allow for the passage of air to facilitate drying of the nasal cannula or other medical equipment. Receptacle 510 may be configured to inhibit the growth of microbes on a piece of medical equipment placed in receptacle 510.

Coupling element 520 may be coupled to back surface 512 and/or front surface 513 of receptacle 510, or any suitable portion of receptacle 510.

Coupling element 520 may include one or more straps 524 coupled to receptacle 510. Straps 524 may be stitched, glued, ultrasonically welded, and/or otherwise irremovably or removably coupled to receptacle 510. Straps 524 may include one or more releasable couplings, such as hook-and-loop fasteners, buttons and/or buttonholes, or any other suitable couplings. Straps 524 may be closed loops or may have free ends 525. Free end 525 of one strap 524 may be releasably coupled to the same strap 524, to receptacle 510, or to another strap 524 coupled to receptacle 510. For example, a hook-and-loop fastener on a free end 525 of one strap 524 may be configured to be coupled to another hook-and-loop fastener on the same strap 524, to a hook-and-loop fastener on receptacle 510, or to a hook-and-loop fastener on a free end 525 of another strap 524 coupled to receptacle 510.

Coupling element 520 may be configured to allow receptacle 510 to be hung from an oxygen tank, oxygen concentrator, rail, or any other suitable location. Coupling element 520 may be configured to hold up to 2 pounds, up to 3 pounds, up to 4 pounds, or up to 5 pounds. Coupling element 520 may be configured to be easily removed. Coupling element 520 may be reusable. Coupling element 520 may be detachable from receptacle 510.

Marking surface 530 may be coupled to front surface 513 of receptacle 510. Alternatively, marking surface 530 may be coupled to back surface 512 of receptacle, or any suitable portion of receptacle 510. Marking surface 530 may be written on with a pen or other writing instrument. Marking surface 530 may include an ink, coating, or material applied to at least a portion of receptacle 510. Marking surface 530 may include a writable ink, a rubberized or plasticized coating, or other material applied to at least a portion of receptacle 510. Alternatively, marking surface 530 may include a label made of paper, fabric, or other suitable material stitched, glued, taped, or otherwise coupled to receptacle 510. Still alternatively, marking surface 530 may include a hang tag tied with a string or otherwise coupled to receptacle 510. Still alternatively, marking surface 530 may be a substantially smooth portion of receptacle 510. Marking surface 530 may be pre-marked with a mark such as "DATE," "NAME," or any other suitable mark.

Marking surface 530 may allow a date to be written on receptacle 510. Marking surface 530 may help indicate for how long a nasal cannula and/or cannula holder 500 has been in use, and may help act as a reminder that a new nasal cannula and/or cannula holder 500 is needed. Marking surface 530 may also allow patient name or any other information to be written on receptacle 510.

Figure 6A:
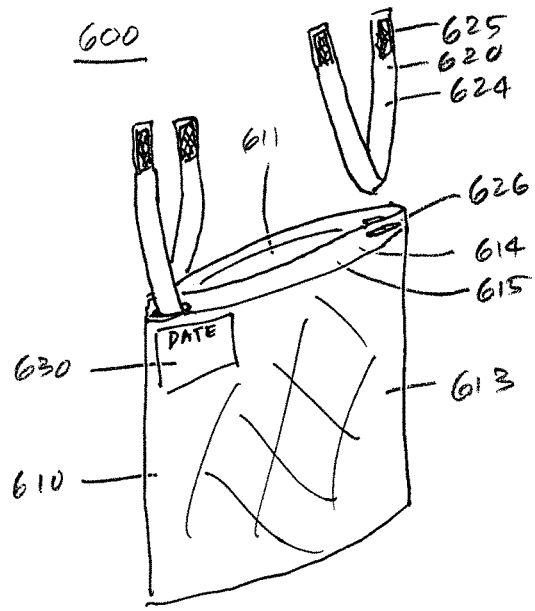
FIGS. 6A-6C show one embodiment of a cannula holder 600.
Figure 6B:
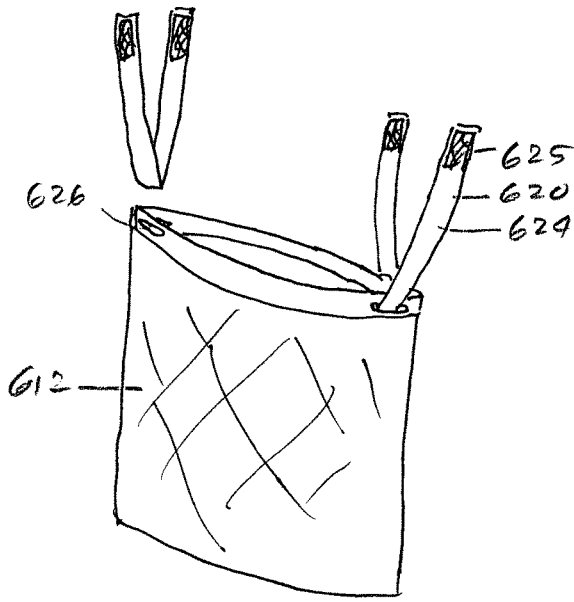
Figure 6C:
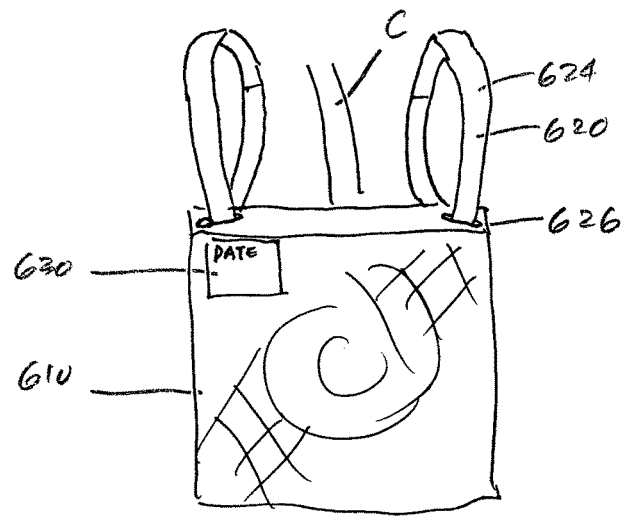

FIGS. 6A-6C show one embodiment of a cannula holder 600. FIG. 6A shows a front view of cannula holder 600. FIG. 6B shows a rear view of cannula holder 600. FIG. 6C shows cannula holder 600 in use with a nasal cannula.

Cannula holder 600 may be configured to hold a nasal cannula. Cannula holder 600 may also be configured to hold a CPAP mask, BPAP mask, nebulizer mask, or any other piece of medical equipment. Cannula holder 600 is configured to help prevent a nasal cannula from coming into contact with unclean surfaces when not in use, helping to keep the nasal cannula clean. Cannula holder 600 prevents a nasal cannula from falling onto the floor or elsewhere when not in use. Cannula holder 600 provides an alternative to placing or hanging a nasal cannula on equipment, furniture, or elsewhere. Cannula holder 600 may be disposable, or may be cleaned and re-used. Cannula holder 600 may be sterilized using gamma sterilization or other methods, and packaged in sterile packaging and removed when ready to be used.

Cannula holder 600 may include a receptacle 610, one or more coupling elements 620, and one or more marking surfaces 630.

Receptacle 610 may include an opening 611, a back surface 612, and a front surface 613. Opening 611 may be configured to receive a nasal cannula.

Opening 611 may be configured to lay flat when not in use. Alternatively, opening 611 may be configured to remain at least slightly open to facilitate the insertion of a nasal cannula. Opening 611 may be kept at least slightly open with a stiffening element 615 such as a metal or plastic wire coupled at or near opening 611.

Receptacle 610 may be rectangular, semicircular, triangular, or any other suitable shape. Receptacle 610 may be capable of being collapsed flat. Receptacle 610 may be configured to conform to a surface or location to which it is intended to be coupled.

Receptacle 610 may be at least partially made of a fabric or material which is breathable. Receptacle 610 may be at least partially made of a fabric or material which encourages the wicking of moisture away from the medical equipment inside receptacle 610, through capillary action and/or other mechanisms. Receptacle 610 may be at least partially made of a fabric or material which encourages the wicking of moisture from an inside of receptacle 610 to an outside of receptacle 610, through capillary action and/or other mechanisms. Receptacle 610 may be at least partially made of a fabric or material with a low surface energy which reduces or discourages the beading or accumulation of moisture.

Receptacle 610 may be at least partially made of a mesh fabric made of polyester, nylon, cotton, or other suitable fabric. The mesh fabric may be breathable and allow air and moisture to escape. The mesh fabric may have a mesh pattern configured to reduce the likelihood of snagging or catching the nasal cannula, CPAP mask, BPAP mask, nebulizer mask, or any other piece of medical equipment. For example, the mesh fabric may have circular or elliptical openings having a size of approximately 0.5 mm to 1.5 mm, with an open area of approximately 30-50%. The mesh fabric may have a mesh pattern and/or color that allows the contents of receptacle 610 to be at least partially visible. The mesh fabric may be a single layer, double layer, triple layer, or any other suitable type of weave that allows airflow but reduces the possibility of snagging on the medical equipment inserted into receptacle 610. The mesh fabric may be made of a material that does not substantially weaken when exposed to moisture. The mesh fabric may be of a weight that is light, medium, heavy, or any suitable combination of weights.

The mesh fabric may be treated with an antimicrobial agent capable of inhibiting the growth of and/or kill microorganisms. The antimicrobial agent may include silver or any other suitable antimicrobial agent. The silver may be in the form of silver nanoparticles bound in a zeolite, calcium carbonate, ceramic, or other suitable matrix, applied to the mesh fabric. The mesh fabric may have inherent antimicrobial properties. The mesh fabric may be treated with hydrophobic, hydrophilic, or other treatments.

Receptacle 610 may be at least partially made of one or more nonwoven fabrics. These fabrics may include spunbond polypropylene fabrics available from DuPont, Surya Textech, Oxco, and others. The polypropylene fabrics may be 100% polypropylene or a polypropylene blend. In one embodiment, a polypropylene blend may include approximately 63% polypropylene, 23% polyethylene terephthalate (PET), 8% viscose fiber, 2% acrylic acid, 1.5% polyamide, and 2.5% other materials. In one embodiment, a polypropylene fabric used may have a weight from approximately 20 GSM to 100 GSM.

Alternatively, receptacle 610 may be at least partially made of a plastic, paper/cellulose, metal, or any other suitable material. Receptacle 610 may be at least partially made of a material that is perforated or non-perforated. Receptacle 610 may be at least partially made of a flexible or rigid material. Any of these materials may be treated with an antimicrobial agent.

Receptacle 610 may be reinforced with a trim 614 along opening 611 and/or one or more edges. Trim 614 may be formed by folding over the fabric one or more times and stitched, glued, ultrasonically welded, and/or otherwise coupled to itself. Alternatively, trim 614 may be a separate piece of fabric. Opening 611 may be kept at least slightly open by shaping trim 614.

Receptacle 610 may be configured to hold a nasal cannula. Receptacle 610 may be configured to enclose all, half, or any portion of a nasal cannula. Receptacle 610 may also be configured to hold a CPAP mask, BPAP mask, nebulizer mask, or any other piece of medical equipment. In one embodiment, receptacle 610 may have a length of approximately 4-15 inches and a width of approximately 4-15 inches. Receptacle 610 may be configured to be breathable to allow for the passage of air to facilitate drying of the nasal cannula or other medical equipment. Receptacle 610 may be configured to inhibit the growth of microbes on a piece of medical equipment placed in receptacle 610.

Coupling element 620 may include one or more straps 624 coupled to receptacle 610. Straps 624 may be passed through one or more strap openings 626 formed through front surface 613 and/or back surface 612 of receptacle 610. Strap openings 626 may be formed at or near the upper corners of receptacle 610, at or near opening 611 of receptacle 610, through trim 614, or any other suitable location. Strap openings 626 may be slit-like, elongate, round, or any other suitable shape. Straps 624 may include one or more releasable couplings, such as hook-and-loop fasteners, buttons and/or buttonholes, or any other suitable couplings. Straps 624 may be closed loops or may have free ends 625. Free end 625 of one strap 624 may be releasably coupled to the same strap 624 or to another strap 624 coupled to receptacle 610. For example, a hook-and-loop fastener on a free end 625 of one strap 624 may be configured to be coupled to another hook-and-loop fastener on the same strap 624 or to a hook-and-loop fastener on a free end 625 of another strap 624 coupled to receptacle 610.

Coupling element 620 may be configured to allow receptacle 610 to be hung from an oxygen tank, oxygen concentrator, rail, or any other suitable location. Coupling element 620 may be configured to hold up to 2 pounds, up to 3 pounds, up to 4 pounds, or up to 5 pounds. Coupling element 620 may be configured to be easily removed. Coupling element 620 may be reusable. Coupling element 620 may be detachable from receptacle 610.

Marking surface 630 may be coupled to front surface 613 of receptacle 610. Alternatively, marking surface 630 may be coupled to back surface 612 of receptacle, or any suitable portion of receptacle 610. Marking surface 630 may be written on with a pen or other writing instrument. Marking surface 630 may include an ink, coating, or material applied to at least a portion of receptacle 610. Marking surface 630 may include a writable ink, a rubberized or plasticized coating, or other material applied to at least a portion of receptacle 610. Alternatively, marking surface 630 may include a label made of paper, fabric, or other suitable material stitched, glued, taped, or otherwise coupled to receptacle 610. Still alternatively, marking surface 630 may include a hang tag tied with a string or otherwise coupled to receptacle 610. Still alternatively, marking surface 630 may be a substantially smooth portion of receptacle 610. Marking surface 630 may be pre-marked with a mark such as "DATE," "NAME," or any other suitable mark.

Marking surface 630 may allow a date to be written on receptacle 610. Marking surface 630 may help indicate for how long a nasal cannula and/or cannula holder 600 has been in use, and may help act as a reminder that a new nasal cannula and/or cannula holder 600 is needed. Marking surface 630 may also allow patient name or any other information to be written on receptacle 610.

Example 1

Figure 7A:
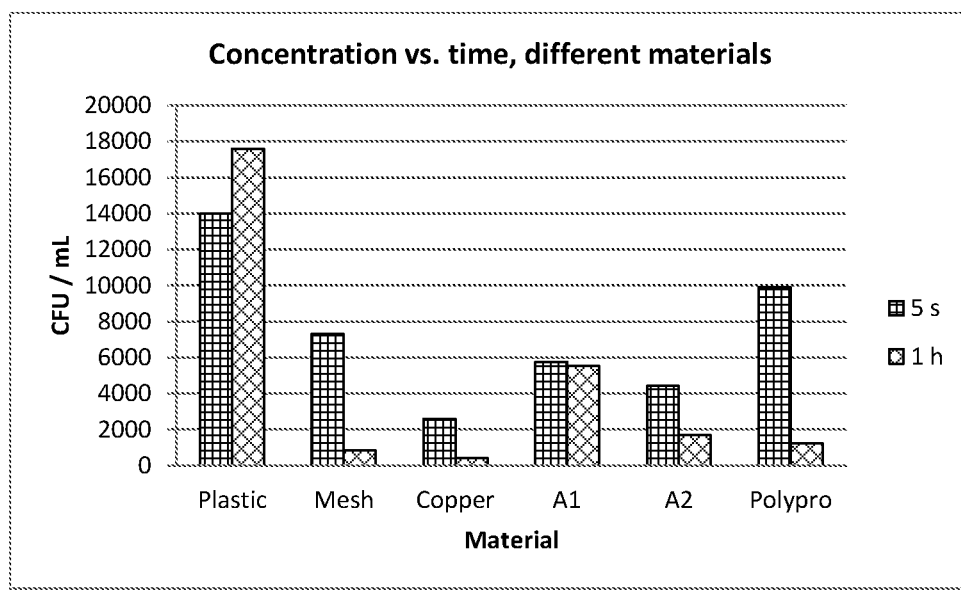
FIGS. 7A-7D show the concentration of a bacteria at versus time for different receptacles.

FIG. 7A shows the concentration of a bacteria at 5 seconds and 1 hour in receptacles made of six different materials: (1) plastic, (2) a mesh fabric, (3) a copper-treated cotton fabric, (4) a first antimicrobial nonwoven fabric (A1), (5) a second antimicrobial nonwoven fabric (A2), and (6) a spunbond polypropylene fabric, 40 GSM.

Multiple pieces of nasal cannula tubing were contaminated with a bacteria, *S. epidermidis*, and placed into each receptacle. After incubation periods of 5 seconds and 1 hour, a piece of tubing was removed from each receptacle and the concentration of bacteria (CFU/mL) estimated. Each estimate is the average concentration of two assays. The data for FIG. 7A are listed in TABLE 1.

TABLE 1

Concentration vs. time, different materials

| Label | Description | Concentration (CFU/mL) | |
|---|---|---|---|
| | | 5 s | 1 h |
| Plastic | Plastic | 14000 | 17600 |
| Mesh | Mesh fabric | 7300 | 840 |
| Copper | Copper-treated cotton fabric | 2600 | 410 |
| A1 | Antimicrobial nonwoven fabric #1 | 5760 | 5520 |
| A2 | Antimicrobial nonwoven fabric #2 | 4420 | 1690 |
| Polypro | Spunbond polypropylene (40 GSM) | 9900 | 1220 |

After one hour, the spunbond polypropylene had an approximately 88% drop in bacteria concentration. This compares to a 25% increase in bacteria concentration in a plastic bag. The performance of the spunbond polypropylene was comparable to that of the mesh fabric (approximately 88% drop) and the copper-treated cotton fabric (approximately 84% drop) in the inhibition of bacteria growth.

Example 2

Figure 7B:
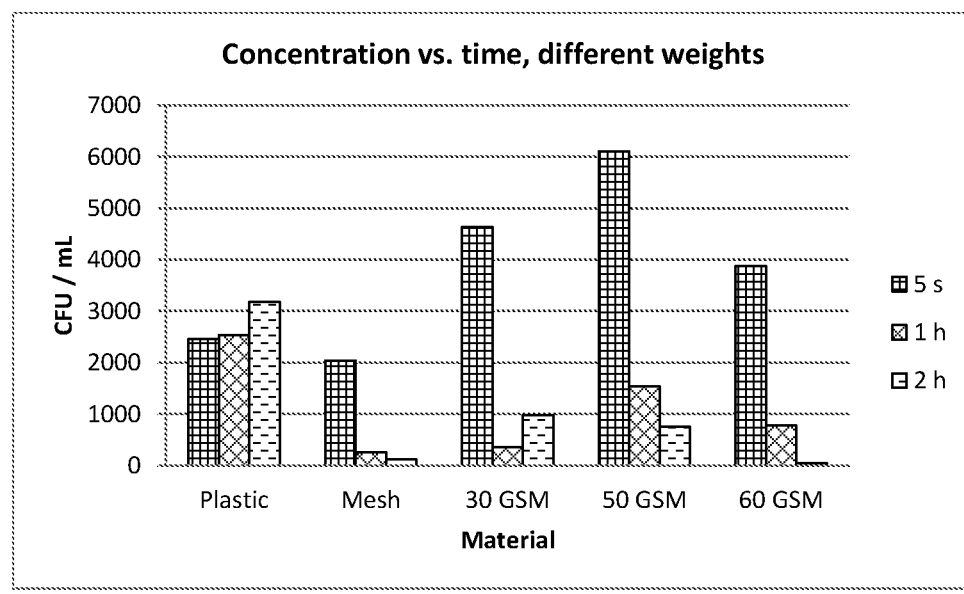

FIG. 7B shows the concentration of a bacteria at 5 seconds, 1 hour, and 2 hours in receptacles made of spunbond polypropylene fabrics of three different weights: 30 GSM, 50 GSM, and 60 GSM. In addition, receptacles made of plastic and a mesh fabric were included for comparison.

Multiple pieces of nasal cannula tubing were contaminated with a bacteria, *S. epidermidis*, and placed into each receptacle. After incubation periods of 5 seconds, 1 hour, and 2 hours, a piece of tubing was removed from each receptacle and the concentration of bacteria (CFU/mL) estimated. Each estimate is the average concentration of two assays. The data for FIG. 7B are listed in TABLE 2.

TABLE 2

Concentration vs. time, different weights

| Label | Description | Concentration (CFU/mL) | | |
|---|---|---|---|---|
| | | 5 s | 1 h | 2 h |
| Plastic | Plastic | 2460 | 2540 | 3180 |
| Mesh | Mesh fabric | 2040 | 260 | 120 |
| 30 GSM | Spunbond polypropylene (30 GSM) | 4640 | 360 | 980 |
| 50 GSM | Spunbond polypropylene (50 GSM) | 6110 | 1540 | 750 |
| 60 GSM | Spunbond polypropylene (60 GSM) | 3880 | 780 | 50 |

After one hour, the three weights had an approximately 92% drop (30 GSM), 75% drop (50 GSM), and 80% drop (60 GSM) in bacteria concentration. After two hours, the three weights had an approximately 79% drop (30 GSM), 88% drop (50 GSM), and 99% drop (60 GSM) in bacteria concentration. The use of heavier weights (50 GSM and 60 GSM) did not have an adverse effect on the inhibition of bacteria growth as compared to the lighter weights (40 GSM from EXAMPLE 1 and 30 GSM).

Example 3

Figure 7C:
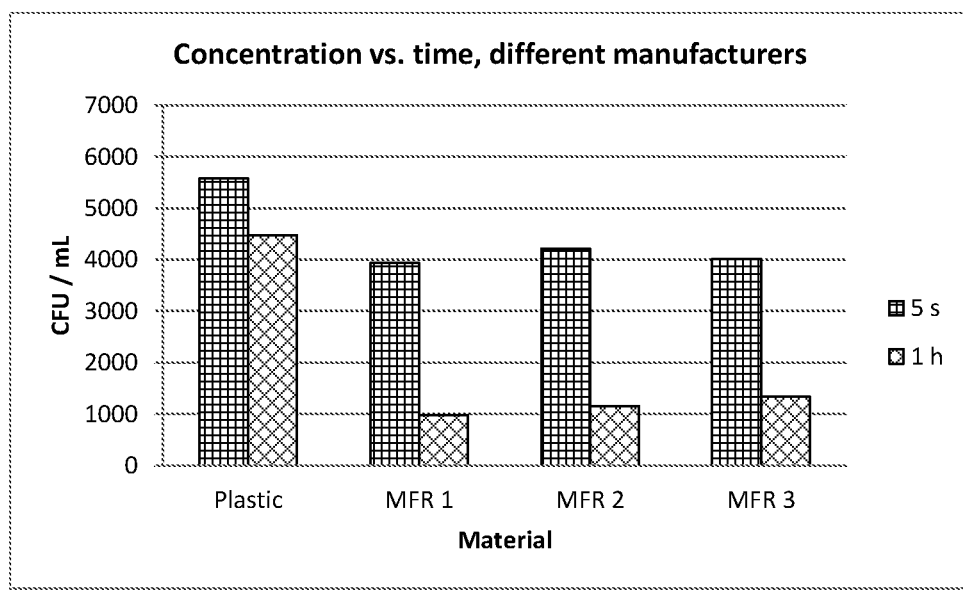
Figure 7D:
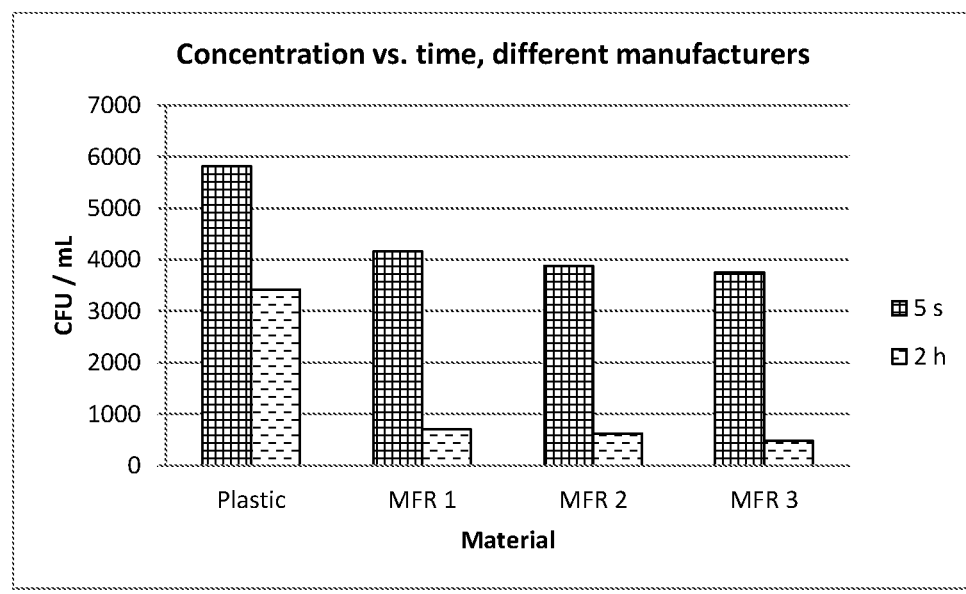

FIGS. 7C-7D shows the concentration of a bacteria at 5 seconds, 1 hour, and 2 hours in receptacles made of spunbond polypropylene fabrics from three different manufacturers: KM Corp., Hwaesong, South Korea (MFR 1); Cangnan Xuantong Craft & Gift Co., Ltd., Wenzhou, China (MFR 2); and Maibao International Group Co., Ltd., Hong Kong (MFR 3). In addition, a receptacle made of plastic was included for comparison. The fabric from KM Corp. (MFR 1) was a polypropylene blend, comprising approximately 63% polypropylene, 23% polyethylene terephthalate (PET), 8% viscose fiber, 2% acrylic acid, 1.5% polyamide, and 2.5% other materials. The fabrics from the other manufacturers were 100% polypropylene.

Multiple pieces of nasal cannula tubing were contaminated with a bacteria, *S. epidermidis*, and placed into two sets of four receptacles. After incubation periods of 5 seconds and 1 hour, a piece of tubing was removed from each of the first set of receptacles and the concentration of bacteria (CFU/mL) estimated. The results for the first set of receptacles is shown in FIG. 7C. After incubation periods of 5 seconds and 2 hours, a piece of tubing was removed from each of the second set of receptacles and the concentration of bacteria (CFU/mL) estimated. The results for the second set of receptacles is shown in FIG. 7D. The data for FIGS. 7C-7D are listed in TABLES 3-4, respectively.

TABLE 3

Concentration vs. time, different manufacturers

| Label | Description | Concentration (CFU/mL) | |
|---|---|---|---|
| | | 5 s | 1 h |
| Plastic | Plastic | 5580 | 4480 |
| MFR 1 | Spunbond polypropylene (MFR 1) | 3940 | 980 |
| MFR 2 | Spunbond polypropylene (MFR 2) | 4220 | 1160 |
| MFR 3 | Spunbond polypropylene (MFR 3) | 4020 | 1340 |

TABLE 4

Concentration vs. time, different manufacturers

| Label | Description | Concentration (CFU/mL) | |
|---|---|---|---|
| | | 5 s | 2 h |
| Plastic | Plastic | 5820 | 3420 |
| MFR 1 | Spunbond polypropylene (MFR 1) | 4160 | 700 |
| MFR 2 | Spunbond polypropylene (MFR 2) | 3880 | 620 |
| MFR 3 | Spunbond polypropylene (MFR 3) | 3760 | 480 |

After one hour, the fabrics from the three manufacturers had an approximately 75% drop (MFR 1), 73% drop (MFR 2), and 67% drop (MFR 3) in bacteria concentration. After two hours, the fabrics from the three manufacturers had an approximately 83% drop (MFR 1), 84% drop (MFR 2), and 87% drop (MFR 3) in bacteria concentration. Especially after two hours, the use of fabrics from different manufacturers did not have a large difference on the inhibition of bacteria growth. Also, the use of a polypropylene blend fabric (MFR 1) did not have an adverse effect on the inhibition of bacteria growth as compared to the 100% polypropylene fabrics (MFR 2, MFR 3).

While the foregoing has been with reference to particular embodiments of the invention, it will be appreciated by those skilled in the art that changes in these embodiments may be made without departing from the principles and spirit of the invention.

What is claimed is:

1. A device for holding a piece of medical equipment, the device comprising:
   a receptacle configured to hold the piece of medical equipment, the receptacle made of a breathable material that allows air, liquid moisture, and gas moisture to pass through, the breathable material configured to wick moisture through capillary action from an inside of the receptacle to an outside of the receptacle; and
   an adhesive tape coupled to an exterior of a back surface of the receptacle, the adhesive tape configured to couple the receptacle to a location, the adhesive tape strong enough to hold the piece of medical equipment.

2. The device of claim 1, wherein the receptacle includes an opening that remains open when in use.

3. The device of claim 1, wherein the receptacle includes a bottom that is closed.

4. The device of claim 1, wherein the breathable material includes a polypropylene fabric.

5. The device of claim 4, wherein the polypropylene fabric comprises a spunbond polypropylene fabric.

6. The device of claim 4, wherein the polypropylene fabric has a weight of approximately 20 GSM to 100 GSM.

7. The device of claim 1, wherein the adhesive tape includes a double-sided adhesive tape.

8. The device of claim 1, further comprising:
a marking surface coupled to the receptacle, the marking surface configured to be written on with a writing instrument.

9. The device of claim 8, wherein the marking surface includes an ink, material, or coating applied to at least a portion of the receptacle.

10. A method for holding a piece of medical equipment, the method comprising:
coupling a receptacle to a location using an adhesive tape, the adhesive tape coupled to an exterior of a back surface of the receptacle, the adhesive tape strong enough to hold the piece of medical equipment, the receptacle configured to hold the piece of medical equipment, the receptacle made of a breathable material that allows air, liquid moisture, and gas moisture to pass through, the breathable material configured to wick moisture through capillary action from an inside of the receptacle to an outside of the receptacle; and
inserting the piece of medical equipment into the receptacle.

11. The method of claim 10, further comprising:
writing on a marking surface coupled to the receptacle.

* * * * *